US006967485B1

(12) United States Patent
Hsueh et al.

(10) Patent No.: US 6,967,485 B1
(45) Date of Patent: Nov. 22, 2005

(54) AUTOMATIC DRIVE ADJUSTMENT OF ULTRAVIOLET LAMPS IN PHOTO-IONIZATION DETECTORS

(75) Inventors: Wenpeng Hsueh, Fremont, CA (US); Weili Yeh, San Jose, CA (US); Peter C. Hsi, Fremont, CA (US); Hong T. Sun, Los Gatos, CA (US)

(73) Assignee: RAE Systems, Inc., San Jose, CA (US)

( * ) Notice: Subject to any disclaimer, the term of this patent is extended or adjusted under 35 U.S.C. 154(b) by 23 days.

(21) Appl. No.: 10/607,950

(22) Filed: Jun. 27, 2003

(51) Int. Cl.[7] .......................... G01N 27/62; G01R 35/00; G01T 1/185

(52) U.S. Cl. ........................ 324/464; 324/601; 324/414; 250/382

(58) Field of Search ................................ 250/374–388, 250/281, 282, 286, 289; 324/404–414, 459–465, 324/601

(56) References Cited

U.S. PATENT DOCUMENTS 5,115,668 A * 5/1992 Welch ........................... 73/52
5,393,979 A 2/1995 Hsi
5,528,288 A * 6/1996 Sandor et al. ................ 348/97
5,561,344 A 10/1996 Hsi
5,703,489 A * 12/1997 Kuroe ........................ 324/601
5,773,833 A 6/1998 Hsi
6,225,633 B1 * 5/2001 Sun et al. ................... 250/389
6,262,542 B1 * 7/2001 Kim et al. .................. 315/224
6,313,638 B1 11/2001 Sun et al.
6,320,388 B1 11/2001 Sun et al.
6,333,632 B1 12/2001 Yang et al.
6,469,303 B1 10/2002 Sun et al.
6,509,562 B1 1/2003 Yang et al.
6,661,233 B2 * 12/2003 Yang et al. ................. 324/464
2002/0171819 A1 * 11/2002 Cheung ...................... 355/133
2002/0179846 A1 12/2002 Sun et al.
2003/0071629 A1 4/2003 Yang et al.
2003/0146082 A1 * 8/2003 Gibson et al. ........... 204/157.3

* cited by examiner

*Primary Examiner*—Anjan Deb
*Assistant Examiner*—Jeff Natalini
(74) *Attorney, Agent, or Firm*—David T. Millers

(57) ABSTRACT

A photo-ionization detector having an adjustable drive power for a UV lamp implements a calibration operation that determines measurement signals for a series of drive power levels and based on the resulting measurement signals selects one or more drive power levels for normal operation of the PID. The calibration operation permits use of UV lamps having a wider range of performance levels and thereby improves manufacturing yields and extends the useful life of the PID. During normal operation, the PID further fine-tunes the drive power level to compensate for expected or measured degradation in lamp performance. Accordingly, between calibrations, the PID maintains a more uniform UV intensity for more accurate measurements. To expand the measurement range of the PID, the calibration process can select two or more power levels for use when measuring different gas concentrations.

3 Claims, 4 Drawing Sheets

AUTOMATIC DRIVE ADJUSTMENT OF ULTRAVIOLET LAMPS IN PHOTO-IONIZATION DETECTORS

BACKGROUND

Photo-ionization detectors (PIDs) can detect and measure the concentrations of volatile gases in a gas sample by ionizing the volatile gases and measuring a resulting ionization current. FIG. 1 illustrates a conventional PID 100 including an ultraviolet (UV) lamp 110, which typically produces high-energy photons having energy above about 8.4 electron volts (eV). The high-energy photons from UV lamp 110 are directed into an ionization chamber 120 through an optical window 116, which may be an integral part of UV lamp 110. When a UV photon collides with a volatile gas molecule having an ionization potential below the energy of the UV photon, the collision ionizes the volatile gas molecule freeing an electron and creating a detectable ion.

An ion detector 130 in PID 100 has a pair of electrodes 132 and 134 that are typically made of a metal. A high voltage (e.g., greater than 150 V) applied between electrodes 132 and 134 generates an electrical field that attracts positively-charged particles (e.g., ions) to electrode 132 and attracts negatively-charged particles (e.g., electrons) to electrode 134. Electrode 134 repels ions towards electrode 132 that is simultaneously collecting the volatile gas ions. As a result, a measurement current produced at electrode 132 indicates the number of ions collected. The magnitude of the measurement current (or a measurement signal generated from the measurement current) therefore depends on the concentration of ionizable gas molecules, the intensity of the UV light in ionization chamber 120, and the efficiency of ion detector 130. If the detector efficiency and the UV light intensity are constant, a one-to-one mapping can be used to convert the measurement signal to a concentration, e.g., in parts per million (ppm) of the volatile/organic compounds.

A conventional PID 100 has a drive circuit 112 that drives UV lamp 110 with a constant amplitude driver signal. However, with a constant driver signal, a variety of factors, including degradation of UV lamp 10, contamination of optical window 116, and the presence of interfering substances such as methane in ionization chamber 120 typically diminish the UV light intensity of UV lamp 110 during normal operation of PID 100.

U.S. Pat. No. 6,225,633 issued to Hong T. Sun and Peter C. Hsi describes a process for self-cleaning a PID and particularly the optical window in the ionization chamber. The self-cleaning process traps air or another gas containing oxygen in the ionization chamber and transmits UV light into the ionization chamber to create ozone. Circulation through the PID is restricted so that the ozone accumulates in the ionization chamber, and ozone, being a strong oxidant, etches and removes the contamination from the optical window and other surfaces in the ionization chamber. Although the cleaning of the window eliminates or reduces one cause of UV intensity reductions, the degradation of the UV lamp still causes the gradual loss of UV light intensity. As a result, the measurement current that a conventional PID detects for a specific gas concentration decreases over time.

FIG. 2 illustrates plots 210, 220, 230, 240, and 250 of the typical dependence of the measurement signal on the volatile gas concentration for several different UV intensities. A calibration operation for a conventional PI) feeds a span gas having a known concentration of volatile gases into the PID, activates the UV lamp, and selects the mapping 210, 220, 230, 240, or 250 that maps the resulting measurement signal to the known concentration of the span gas. The mapping selected during calibration is then used for measurements during normal operation. However, as a PID ages, the UV intensity from the lamp drops, and the selected mapping of the measurement signal to the gas concentration becomes inaccurate. To prevent drift in the concentration measurements, a conventional PID thus requires frequent calibration to reselect the correct mapping for the conversion of measurement signals to volatile gas concentrations.

SUMMARY

In accordance with an aspect of the invention, a photo-ionization detector (PID) adjusts the lamp power level to keep the UV intensity in a range required for measurements. These adjustments increase the sensitivity of a detector containing a weak or degraded lamp and extend the life of the lamp by permitting use of the lamp even after a significant drop in output UV intensity. The adjustments can also improve measurement stability over a longer period of time without requiring more frequent calibrations and avoid loss of lamp operation that might otherwise result in a complete loss of measurement and detection functions.

A calibration process can improve manufacturing yields since the power setting of lamps that are brighter or dimmer than normal can be calibrated to provide a UV intensity in the desired range. In particular, varying the driving power can increase the UV light intensity from a weak lamp and lower the UV intensity from a strong lamp to stop the measurement signal from saturating. In contrast, a conventional PID uses constant power to drive a UV lamp and cannot use UV lamps that are too bright or too dim. Thus, for conventional PIDs, some weak lamps and some strong lamps must be discarded even though the lamps might otherwise have a long operating life.

During an exemplary embodiment of a calibration process, a PID steps through a range of driving power levels while a span gas is in the ionization detector. The PID records the measurement signals for the different driving power levels. At the end of the calibration process, the PID picks the best mapping for conversion of the measurement signal of the PID to a volatile gas concentration and sets the lamp drive power at the level corresponding to the best mapping.

A maintenance process in accordance with an embodiment of the invention fine-tunes the lamp drive power during the periods between calibrations. In particular, the maintenance process can step up the lamp drive power at a rate that compensates for the expected rate of drop in the useful UV intensity from the UV lamp. The expected rate of drop in intensity can be determined for a specific PID under specific operating conditions. The UV intensity drop in a self-cleaning PID, which removes contaminants from the lamp, may be easier to characterize since the drop depends primarily on the aging characteristics of the lamp and not on contamination.

The maximum total increase in the drive power during the maintenance process can be capped, so that after the maintenance process adjusts the lamp drive power to the capped level, the lamp drive power remains constant until the next calibration process. In accordance with one embodiment of the invention, coarse steps in the lamp drive level that are used during calibration are divided into finer steps that are used during the maintenance process. The maintenance process then gradually increases the drive power by the fine steps to maintain the UV light intensity or at least slow the rate of intensity drop. When the accumulation of fine steps reaches the next coarse step, further drive power increases are stopped until a calibration is performed.

In accordance with yet another aspect of the invention, a detector such as a PID controls the drive power of a lamp according to the measured level of detected gases. In particular, a PID can operate a UV lamp at a relatively high drive power setting when the measured voltage gas concentrations are below a selected threshold (e.g., below 100 ppm), but when the measured concentration rises above the threshold concentration level, the PID lowers the drive power of the lamp. The lower drive power saves power and extends the operating period between recharging or replacing batteries in the PID. Although the absolute measurement sensitivity decreases at the lower drive power, sensitivity as a percentage of the measured concentration still remains acceptable.

A failure prevention process increases drive power in response to an indication that the UV lamp is not operating. Complete loss of measurement functions are thus prevented even when lamp aging or the operating environment disables lamp operation at the factory-set power level or previously calibrated power level.

One specific embodiment of the invention is a calibration process for a detector such as a PID. The calibration process includes: (a) selecting a drive signal; (b) applying the selected drive signal to a lamp such as a UV lamp; and (c) recording a measurement signal resulting from ionization that arises from exposing a gas mixture to output from the lamp. Steps (a), (b), and (c) can be repeated until the measurement signals for all drive signals in a predetermined set have been recorded. After the set of measurement signals are recorded, the calibration process selects for normal operation of the detector, the drive signal that corresponds to a desired mapping of measurement signal levels to concentrations of ionizable gases. As an option, the calibration process can further include selecting the desired mapping from among a set of mappings that map the recorded measurement signals to a gas concentration known to be in the gas mixture.

The drive signals in the predetermined set generally differ from each other in amount of drive power provided to the lamp. Each of the drive signals can be, for example, an AC signal, where the drive signals differ in duty cycle or voltage amplitude. As a result, the drive signals cause the lamp to output different UV intensities.

Another specific embodiment of the invention is a process for operating a detector such as a PID. The operating process includes: changing the drive power to a new level after an operating time of the detector indicates that intensity of the output of the lamp may have changed; generating the measurement signal from ionization that arises when exposing sample gas to the output from the lamp operated at the new level; and determining a concentration of the ionizable gases using the measurement signal generated and a mapping of measurement signal levels to concentrations of the ionizable gases.

Changing the drive power typically means increasing the drive power to compensate for expected degradation of performance of the lamp. The changing of the drive power can be repeated at intervals during operation of the detector and typically occurs between consecutive calibrations of the detector. The changes in the drive power are generally less than a difference between the initial level and a next higher level used during the calibration process and can be stopped when an accumulation of changes is equal to or greater than a difference between the initial level and a next higher level used during calibration.

Yet another specific embodiment of the invention is a process for operating a photo-ionization detector that includes (a) applying a first drive signal to a lamp; (b) measuring ionization resulting from exposing a gas mixture to output from the lamp; (c) determining whether the ionization measured indicates the gas mixture contains a concentration of ionizable gas that is above a threshold level; and (d) in response to the concentration being above the threshold level, applying a second drive signal to the lamp and repeating steps (b) and (c). The detector can then switch between two or more drive signals according to gas concentrations being measured.

Another specific embodiment of the invention is a process for operating a photo-ionization detector avoids a total failure by sensing whether a lamp in the detector is operating properly when a first drive signal is applied, and in response to the lamp not operating properly, applying a second drive signal that provides more power to the lamp than does the first drive signal.

Yet another specific embodiment of the invention is a photo-ionization detector implementing any one or more of the above processes.

BRIEF DESCRIPTION OF THE DRAWINGS

Use of the same reference symbols in different figures indicates similar or identical items.

DETAILED DESCRIPTION

In accordance with an aspect of the invention, a photo-ionization detector has an adjustable drive power setting for the UV lamp and operates to change the drive power setting during calibration and normal operation. The calibration process using adjustable power settings during the manufacture of a PID provides greater tolerance for UV lamps having different intensity output and therefore permits use of lamps that may be unsuitable for a PID having a fixed drive power. During use of the PID, the calibration processes extend the useful life of UV lamps by increasing the drive power as needed to keep the UV intensity at a level that provides the required measurement sensitivity. Otherwise, a UV lamp operated at a fixed power level has an output UV intensity that can drop below the UV intensity required for the desired measurement sensitivity.

In accordance with another aspect of the invention, a maintenance process during normal operation of a PID fine-tunes the drive power of a UV lamp in accordance with predicted changes in the performance of the UV lamp. Thus, between calibrations, the drive power of a UV lamp can be increased to compensate for predictable decreases in the useful UV intensity output from the lamp. The drive power adjustments improve measurement accuracy and reduce drift in the measured values by reducing the UV intensity decreases that normally occur during use of a PID.

In accordance with yet another aspect of the invention, normal operation of a PID drives a UV lamp at a power level selected according to the expected or measured volatile gas concentrations. The UV lamp can thus be operated at a minimum power level required to provide a measurement sensitivity that is a desired percentage of the volatile gas concentration. In alternative embodiments, the power level can be user set according to the volatile gas concentrations of interest or dynamically set during operation according to current volatile gas concentration measurements.

Figure 3A:
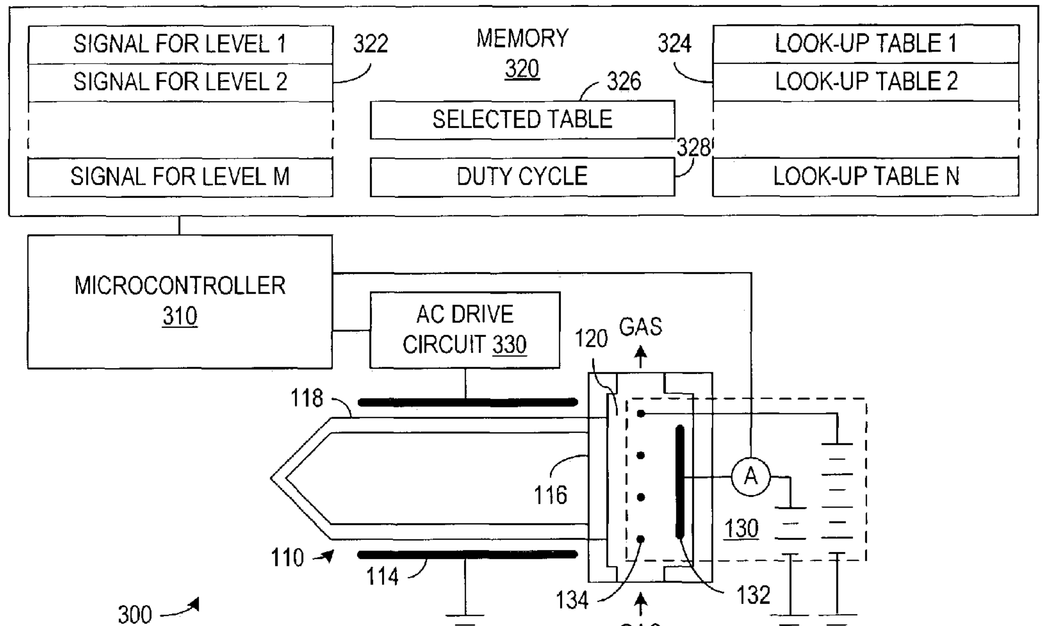
FIGS. 3A, 3B, and 3C are circuit diagrams of PIDs in accordance with alternative embodiments of the invention having an adjustable lamp drive power.

FIG. 3A shows a PID 300 in accordance with an exemplary embodiment of the invention. PID 300 includes a UV lamp 110, an ionization chamber 120, and ion detector 130 that can be conventional in design and implementation. PID 300 further includes a microprocessor or microcontroller 310 such as a Motorola 68HC11 microcontroller that controls the general operation of PID 300 and particularly controls the drive power that an AC drive circuit 330 applies to UV lamp 110. Microcontroller 310 has a memory 320 that may include volatile memory for temporary data storage and nonvolatile memory for storage of firmware and system parameters. Memory 320, although being shown as separate from microcontroller 310, may actually be embedded in microcontroller 310.

PID 300 has a UV lamp 110 that generates UV light through a glow discharge in a gas such as He, Ne, or Kr or a gas mixture that is trapped in a glass tube 118. To induce glow discharge, microcontroller 310 controls application of voltage to conductive electrodes 114 that are outside glass tube 118, and the resulting alternating electric field excites atoms trapped in glass tube 118.

In a typical configuration for PID 300, an AC power signal applied to electrodes 114 has a voltage amplitude VDR of about 500 to 1300 Vpp, a frequency of about 200 KHz, and a duty cycle that is variable between about 30% and 80%. Microcontroller 310 can vary the drive power of UV lamp 110 by varying the duty cycle of the AC drive signal used in AC drive circuits 330 to thereby change the drive signal to UV lamp 110 and the resulting UV intensity output from UV lamp 110. Alternatively, the voltage amplitude or frequency of the drive signal can be changed to alter the UV intensity. In PID 300, microcontroller 310 sets the drive power writing to a memory location or register 328 in memory 320.

Figure 3B:
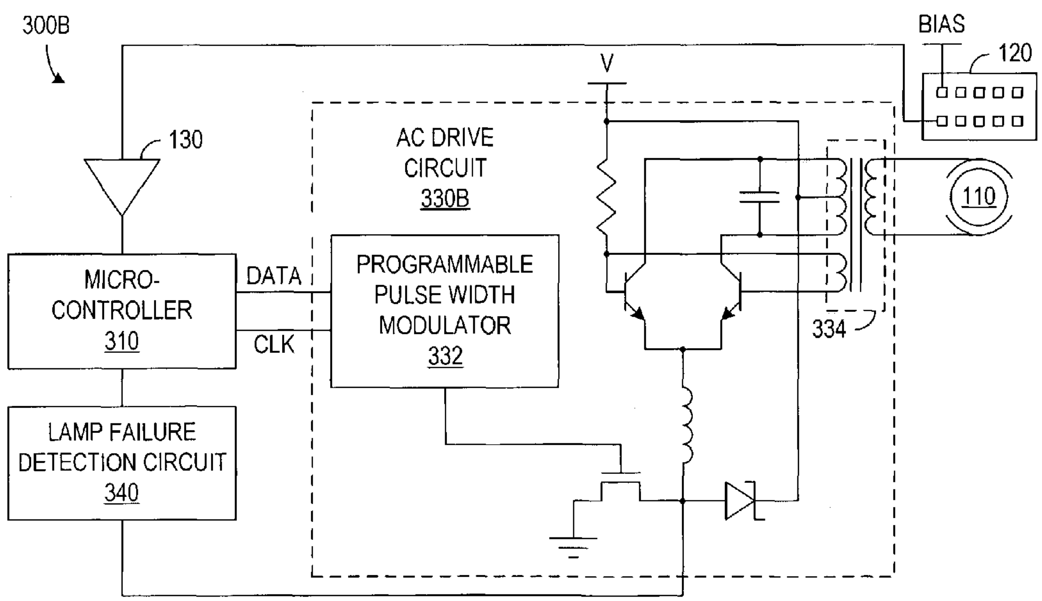

FIG. 3B shows a PID 300B having an AC drive circuit 330B that can be operated using a variable duty cycle. AC drive circuit 330B particularly contains a programmable pulse width modulator 332 that receives a data signal and a clock signal from microcontroller 310 and a transformer 334 that drives lamp 110. Pulse width modulator 332 turns on the current through an oscillator circuit connected to transformer 110 for a time that depends on the duty cycle that microcontroller 310 selected. A change in the duty cycle changes the voltage amplitude that transformer 334 applies to UV lamp 10, and the voltage amplitude changes UV intensity.

Figure 3C:
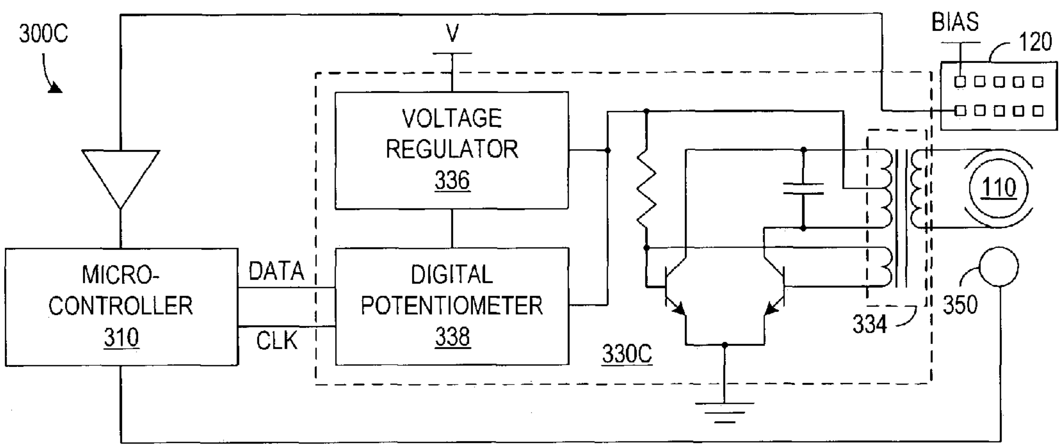

FIG. 3C shows a PID 300C having an AC drive circuit 330C that changes the drive signal to UV lamp 110 by changing the DC voltage applied to an oscillator circuit. AC drive circuit 330 includes a voltage regulator 336 and a digital potentiometer 338. Microcontroller 310 is connected to control the setting of digital potentiometer 338, and the setting of digital potentiometer 338 controls the output voltage that voltage regulator 336 applies to the oscillator circuit. Transformer 334, which is connected to the oscillator circuit, drives lamp 110 with a drive signal having a voltage amplitude that depends on the setting of digital potentiometer 338. The UV intensity thus depends on the setting.

In accordance with an aspect of the invention, the adjustable drive power level for UV lamp 110 can be used to ensure that UV lamp 110 is operating. For this purpose, PID 300B of FIG. 3B includes a lamp failure detection circuit 340 that senses the operation of the oscillator circuit to determine whether UV lamp 110 is responding to drive circuit 330B as expected. (Feedback through transformer 334 changes depending on whether there is glow discharge in UV lamp 110.) Generally, the minimum power or voltage required for glow discharge changes according to the operating environment or the age of UV lamp 110. When failure detection circuit 340 indicates UV lamp 100 is not operating properly, microprocessor 310 can boost the drive power to avoid a complete loss of measurement functions.

PID 300C of FIG. 3C includes a light sensor 350 that measures the light intensity output from WV lamp 110. Microcontroller 310 can monitor light sensor 350 and boost the drive power to UV lamp 110 when necessary to guarantee that UV lamp 110 is operating and to avoid complete loss of measurement functions.

Even if a PID lacks a failure detection circuit or a light sensor for checking lamp operation, a lamp failure can be detected from the difference between the measurement signal at the selected lamp drive level and the measurement signal at a higher lamp drive level (e.g., the maximum drive level.) A disparity in the resulting measurements of volatile gas concentration may indicate a failure of the UV lamp at the lower drive level, which can be corrected by using the higher drive level.

Figure 4:
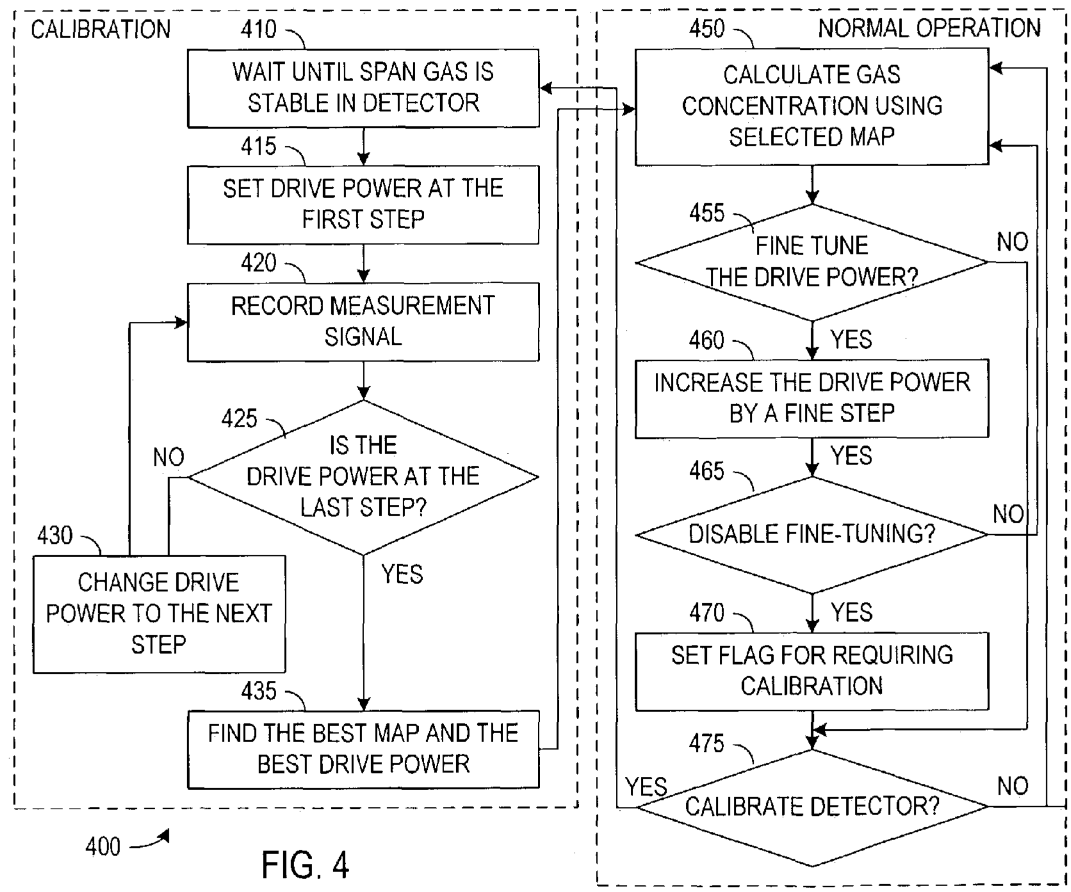
FIG. 4 is a flowchart of PID operation including adjustment of lamp drive levels during calibration and maintenance processes.

FIG. 4 is a flow diagram of a process 400 for operating a PID. Process 400 can generally be conducted in a PID under the control of a microprocessor or microcontroller built into the PID as illustrated in FIG. 3A, 3B, or 3C, in which case, flow diagram 400 represents the action of software or firmware executed within the PID. Alternatively, part of process 400 can be conducted using external equipment available during the manufacture or calibration of the PID.

Process 400 begins with a calibration process that can be conducted during initial assembly of the PID or after normal operation of the PID. For the calibration process, a span gas having a known concentration of volatile gases of the type to be detected are introduced into the PID. A typical span gas for a detector of organic gases may contain a carrier gas such as air mixed with isobutylene at a concentration of about 100 ppm.

The calibration process initially waits in step 410 until the span gas is stable in the PID. A pump or other external equipment can be used to feed the span gas into the PID so that the volatile gas concentration in the PID remains constant throughout the calibration process. Step 415 then sets the drive power of the UV lamp in the PID to a first power setting (e.g., the lowest power level). In PID 300, for example, microcontroller 310 sets the power level by writing a power setting to the AC drive circuit 330.

Once the drive power is set in step 415, a measurement signal is generated and recorded in step 420. Generally, the recorded value can be a direct measurement of the ion current resulting from ionization in the span gas, or the ion current can be converted to a voltage that is measured and recorded. PID 300 can conduct the recording step 420 by digitizing the measurement signal from detector 130 and writing the digital measurement to a memory location 322 corresponding to the current drive power level.

A decision step 425 of the calibration process determines whether a measurement has been recorded for the last power level (e.g., the highest level). If the drive power has not reached the last level, the calibration process branches to a step 430 where the drive power is changed (e.g., incremented) to the next level. Step 420 is then repeated to record a measurement signal that corresponds to the new drive power level.

The changing of the drive power in step 430 and the recording of the measurement signal in step 420 are repeated until decision step 425 determines that a measurement signal value has been recorded for the last drive power level. At this point, the PID has measured a constant volatile gas concentration using several different drive power levels and recorded the resulting measurement signal values.

Step 435 uses the recorded measurement signal values to select the best power level for the UV lamp and the best mapping of the measurement signal levels to volatile gas concentrations. Selecting the best power level can include identifying the mappings that map the recorded measurement signal values to the known span gas concentration and then selecting the best one of the identified mappings (e.g., the mapping having the best measurement sensitivity for the desired range of volatile gas concentrations). Step 435 can then select the power level that corresponds to the best of the identified mappings.

Figure 1:
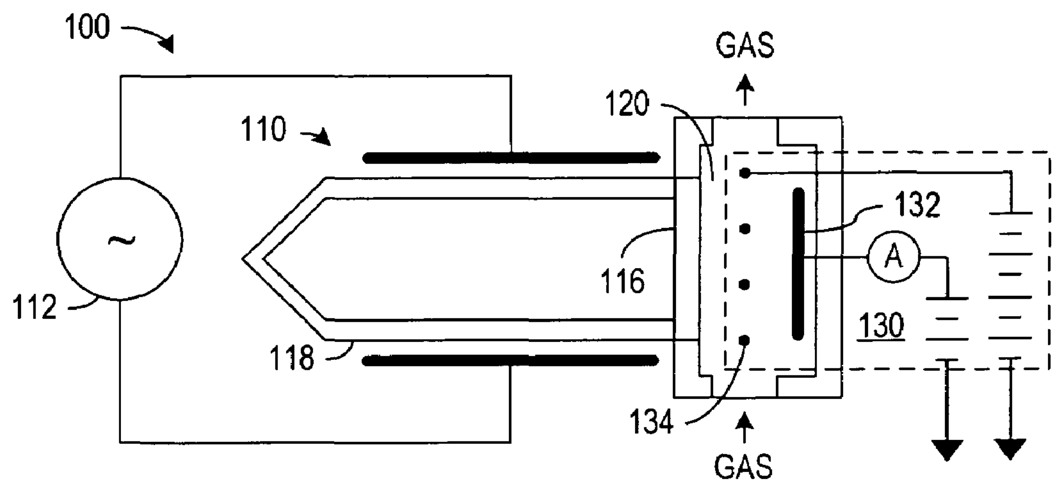
FIG. 1 is a block diagram of a conventional photo-ionization detector (PID).
Figure 2:
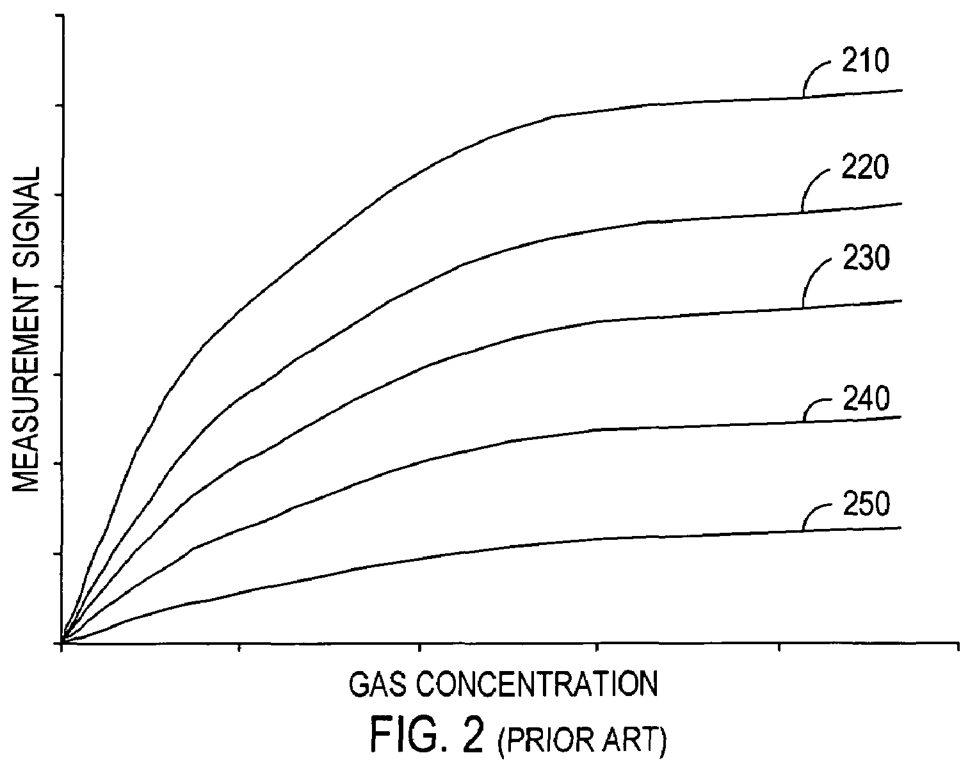
FIG. 2 shows typical plots of the resulting measurement signal as a function of gas concentration for a typical PID.

In PID 300, a non-volatile portion of memory 320 includes a set of look-up tables 324 that represent the mappings between the measurement signal levels and the volatile gas concentrations for several different UV intensities. FIG. 2 qualitatively illustrates a typical set of mappings 210 to 250. The mappings 210 to 250 and look-up tables 324 generally depend on the characteristics of PID 300 such as the geometry of UV lamp 110, ionization chamber 120, and detector electrodes 132 and 134. Use of one or more of the mappings (e.g., mappings 220 and 230) may be preferred for providing a dynamic range for the measurement current that avoids saturation and provides the desired measurement sensitivity or concentration resolution over a target range of volatile gas concentrations.

PID 300 can execute step 435 by finding for each stored measurement 322, the look-up table 324 that maps the stored measurement value 322 to the known concentration of volatile gases in the span gas. This identifies a subset of look-up tables 324 corresponding to the UV lamp drive power levels. The best performing of the identified look-up tables can then be selected, e.g., based on a predetermined ranking of the look-up tables. The drive power level is then set to correspond to the look-up table selected for PID 300. In particular, for PID 300B, a duty cycle that provides a measurement signal on a desirable mapping of measurement signal values to concentrations is stored in non-volatile storage for use during normal operation of PID 300B.

After the calibration process selects a power level and a mapping, normal operation of the PID can begin. Step 450 of FIG. 4 illustrates normal operation in which an ionization current is measured and converted to a volatile gas concentration using the mapping (or the look-up table) identified during the last calibration of the PID.

A decision step 455 decides whether the PID is due for a maintenance process that fine-tunes the drive power of the UV lamp. A maintenance process may be due if maintenance processes are enabled and a condition triggering the maintenance process occurs. In one embodiment of the invention, the decision of whether maintenance is due is based on the operating time since the last calibration or maintenance process was performed in the PID. For example, the maintenance process can be conducted after a fixed interval of operation of the PID or after variable time intervals selected according to expected degradation of lamp performance.

In some applications, the firmware inside a PID can learn from consecutive calibrations and decide how or when to compensate for the changes that UV lamp degradation and environmental contamination cause. In particular, the time between maintenance processes can be selected according to the difference or differences in the power levels selected in the previous two or more calibration operations. The learning process can provide more accurate fine tuning of the drive power because the learning process selects the timing of maintenance operation for the particular PID according to the measured performance in the actual operating environment. Unlike a predict rate of UV lamp degradation, which may be obtained in a lab, this method also includes the variables present in the real environment.

Zero baseline drift can also trigger the maintenance process. Generally, a zero baseline, which corresponds to the measurement signal resulting from measuring a zero gas (i.e., a sample free of ionizable volatile gases), is set during zero calibration of a PID. (The zero baseline can be subtracted from the measurement signal value before using a mapping or look-up table to convert the difference to a volatile gas concentration value.) UV lamp degradation will generally lower the zero baseline. By fine-tuning the lamp drive when the zero baseline changes, a PID can maintain zero baseline within acceptable range and also boost the UV intensity for higher concentration measurement. In particular, if the measurement signal falls significantly below the zero baseline during normal operation of the PID, the drive power to the UV lamp can be increased to compensate for a presumed drop in UV intensity. To determine the zero drift allowed before triggering a maintenance process, a PID can permit a measurement signal that is below the zero baseline by a fixed absolute amount or by a fixed percentage of the difference between the zero baseline and the measurement signal for the span gas. Allowing a fixed absolute amount of zero baseline drift will generally result in different amounts (PPM) of drift in the measured volatile gas concentration for different measurement sensitivities. Allowing a percentage drift in the zero baseline will generally limit the drift in the measured concentration to a constant amount (PPM) even if the sensitivity changes.

Alternatively, a PID such as PID 300C containing a light sensor can trigger the maintenance process when the measured intensity falls by a predetermined amount.

If the PID is due for the maintenance process, step 460 increases the drive power by a relatively fine step to compensate for an expected or measured drop in the UV intensity output from the lamp. The fine step may be, for example, about 10% of the coarse steps between the power levels used during the calibration process.

If the UV intensity is not directly measured, the time between increasing the drive power and the amount of the increase are generally related to each other, so that the drive power increase compensates for the expected drop in the UV intensity. For example, the average drop in UV intensity from UV lamps during a particular interval after the last calibration or maintenance process can be found experimentally or otherwise, and the drive power increase in step 460 can be equal to the increase required to undo the average UV intensity drop. Longer intervals between maintenance processes generally allow larger drops in UV intensity and therefore require larger increases in the drive power. On average, the UV intensity is thus maintained at the level required for the previously selected mapping between the measurement signal and the volatile gas concentration. Alternatively, the drive power increase in step 460 can be less than the increase required to undo the average UV intensity drop to avoid overcompensating for UV intensity drops. Even when the drive power increase does not fully compensate for the UV intensity drop, the drive power increase provides at least partial compensation, which improves measurement accuracy when compared to conventional PID having fixed drive power.

After incrementing the drive power level in step 460, decision step 465 decides whether to disable further fine-tuning in the drive power. The fine-tuning should generally be disabled to prevent unabated or unacceptable increases in the drive power. In an exemplary embodiment of the invention, further fine-tuning is disabled when the accumulated increases in repetitions of step 460 have raised the drive power level from the drive power level selected during the last calibration to a drive power level equal to or greater than the next higher drive power level evaluated during the calibration process. In other words, when the accumulated fine steps in the drive power during repetitions of step 460 are equal to one coarse step in the drive power as used in the calibration. Decision step 465 could alternatively use other criterion such as the absolute magnitude of the drive power level or the time since the last calibration to determine whether to disable further fine-tuning.

If step 465 does not disable fine-tuning, normal operation continues in step 450 and may further fine-tune the drive power of the UV lamp in step 460 when step 455 triggers a maintenance process. If step 465 disables fine-tuning, step 470 sets a flag indicating that calibration of the PID is recommended, and a user can decide in step 475 whether or not to recalibrate the PID.

The maintenance process can provide more accurate measurements particularly in applications where frequent calibration is not acceptable. In fixed systems, where a PID may be in an area that is difficult to access or infrequently accessed, six to twelve months between calibrations may be normal. The maintenance process can avoid the drift or increasing error in measurements that might otherwise occur in infrequently calibrated PIDs.

In accordance with another aspect of the invention, a PID can use multiple power levels and associated mappings to provide an expanded dynamic range of concentration measurements. The drive power of a UV lamp can then be varied according to the volatile gas concentration being measured. In particular, instead of maintaining the highest sensitivity for accurate measurement at low concentration, dimming the UV lamp, which lowers the measured sensitivity, also prevents saturation of the measurement signal at high volatile gas concentrations to cover a wider range at high concentrations. For example, a PID may have 10 raw counts for 1 ppm volatile gas concentration and provide a resolution around 0.1 ppm, but the ion detector may saturate at about $10^5$ counts, which corresponds to a volatile gas concentration of about 1,000 ppm. If the UV intensity is lowered to provide 1 raw count for 1 ppm, which gives a resolution of 1 ppm, the saturation concentration ($10^5$ raw counts) corresponds to about 10,000 ppm. With proper lamp control of the lamp drive, the PID can thus provide a 0.1-ppm resolution for concentration measurements in a range from 0.0 ppm to 999.9 ppm and a 1-ppm resolution for concentration measurements in a range from 1,000 to 10,000 ppm. In this example, every raw count causes less than 0.1% fluctuation in the measurements over 1,000 ppm. In typical applications, higher accuracy (e.g., to one-tenth ppm) is unnecessary for concentration measurements over 1,000 ppm.

Figure 5:
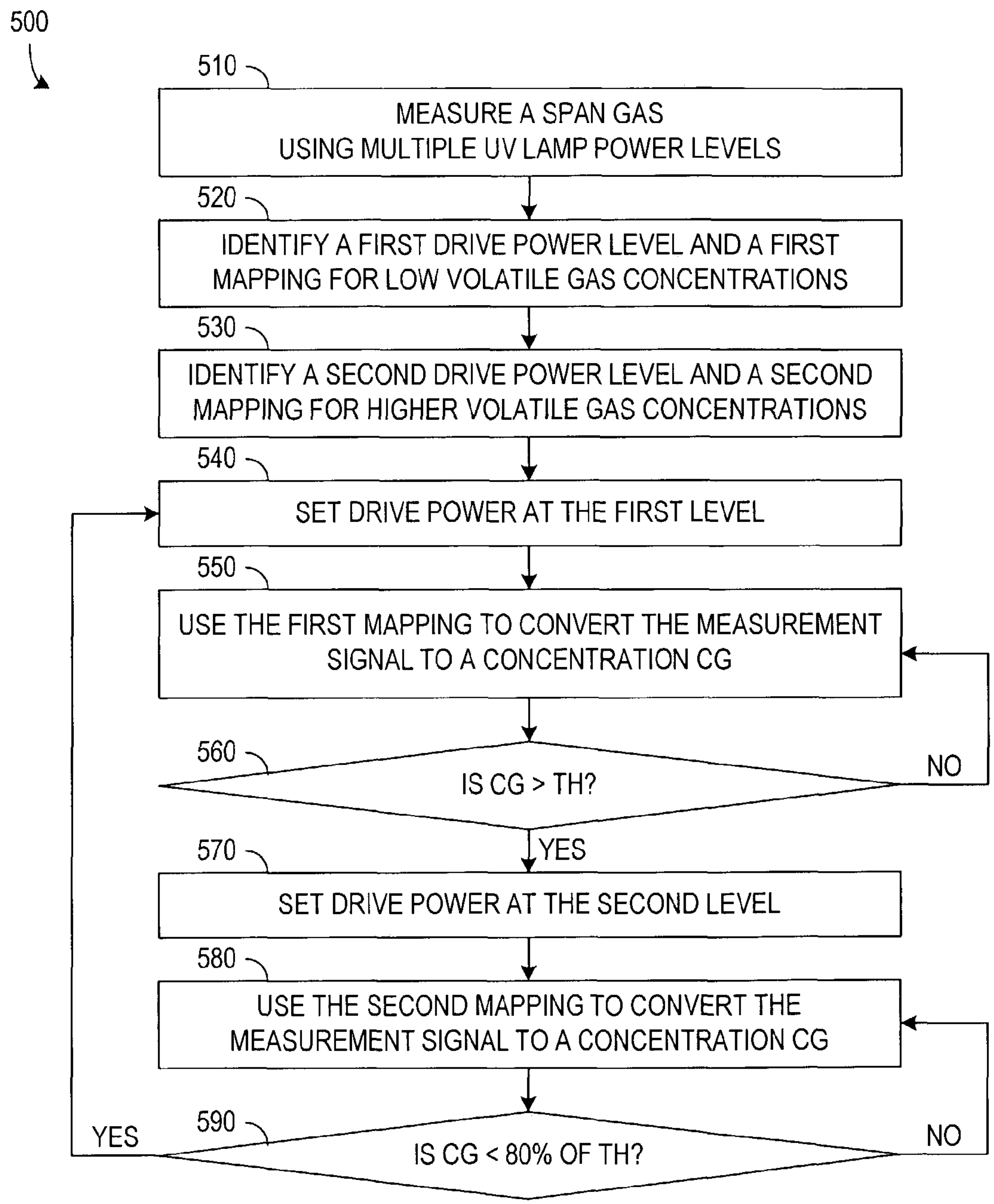
FIG. 5 is a flowchart for a PID that changes the lamp drive power according to the volatile gas concentration being measured.

FIG. 5 is a flow diagram of an operating process 500 for a PID using two different lamp power levels to extend the dynamic range of volatile gas concentration measurements. For process 500, a PID is calibrated in step 510 using a span gas that is measured using a series of lamp drive levels as described above. A first drive power level that corresponds to a mapping that provides the desired measurement sensitivity at low volatile gas concentrations (e.g., 0 to 100 ppm) is selected from the series of drive levels. The lamp drive level and the first mapping are recorded in the PID in step 520. Step 530 selects a second drive power level, which is lower than the first power level but which avoids saturating the PID electronics until a much higher volatile gas concentration (e.g., at a desired maximum of the dynamic measurement range.) The second power level corresponds to a second mapping of the measurement signal levels to volatile gas concentrations, and the second power level and the second mapping are also recorded for use in the PID.

Alternative embodiments of the invention can select power levels for operation of a PID in a variety of different ways. For example, instead of selecting just two power levels and associated mappings, a calibration of a PID can select three or more different power levels and mappings for use at different volatile gas concentrations. Additionally, instead of relying on a single span gas for the calibration, measurements of span gases having different concentrations can be used to select the different power levels. In particular, measurements of a first span gas having low volatile gas concentration can be used for selection of the first drive power used for low concentration measurements, and measurements of a second span gas having high volatile gas concentration can be used for selection of the second drive power used for high concentration measurements.

Once the power levels are selected, process 500 in step 540 sets the drive power of the UV lamp at the first (i.e., the highest) power setting and then in step 550, uses the first mapping to convert the resulting measurement signal level to a volatile gas concentration CG. A decision step 560 then determines whether the volatile gas concentration CG is greater than a threshold concentration TH (e.g., greater than 100 ppm). If not, the PID is measuring a low volatile gas concentration, and process 500 continues to use the present power setting and branches back to step 550 to convert the measurement signal using the first mapping.

If step 560 determines that the voltage gas concentration is above the threshold level TH, the PID in step 570 decreases the drive power of the lamp to the second power level. Step 580 then converts the measurement signal to a volatile gas concentration using the second mapping of the measurement signal level to volatile gas concentration. A decision step 590 then determines whether the volatile gas concentration CG is less than a certain percent of threshold concentration TH (e.g., less than 80 ppm). If not, the PID is measuring a high volatile gas concentration, and process 500 continues to use the second power setting and branches back to step 580 to convert the measurement signal using the second mapping.

If a volatile gas concentration measurement falls below the selected percentage of threshold TH, process 500 branches from step 590 back to step 540 and resets the drive power back to the first drive power level. In this manner, the PID uses the adjustable lamp drive power to extend the dynamic range of measurements while maintaining a desired percentage measurement resolution.

Although the invention has been described with reference to particular embodiments, the description is only an example of the invention's application and should not be taken as a limitation. For example, although the above includes separate descriptions of a PID that fine tunes lamp drive power separately and a PID that uses different lamp power levels for different gas concentration, the aspects of the current invention can be used together. In particular, a maintenance process can fine tune two or more power levels independently or by the same absolute or percentage amount as required to reduce or avoid measurement drift between calibration operations. Various other adaptations and combinations of features of the embodiments disclosed are within the scope of the invention as defined by the following claims.

We claim:

1. A process for operating a detector comprising:

(a) generating a measurement signal from ionization that arises when exposing sample gas to output from a lamp operated at an initial level of a drive power;

(b) determining a concentration of ionizable gases using the measurement signal generated in step (a) and a mapping of measurement signal levels to concentrations of the ionizable gases;

(c) changing the drive power to a new level in response to a trigger event that indicates that intensity of the output of the lamp may have changed;

(d) generating the measurement signal from ionization that arises when exposing sample gas to the output from the lamp operated at the new level;

(e) determining a concentration of the ionizable gases using the measurement signal generated in step (d) and the mapping of measurement signal levels to concentrations of the ionizable gases; and repeating steps (c), (d), and (e) at intervals during operation of the detector, wherein repeating steps (c), (d), and (e) occurs between consecutive calibrations of the detector, wherein each calibration of the detector comprises:

(a1) selecting a coarse level from a plurality of coarse levels for the drive power;

(b1) applying the drive power at the selected coarse level to the lamp;

(c1) recording the measurement signal generated from ionization that arises from exposing a gas mixture to the output from the lamp at the selected coarse level;

(d1) repeating steps (a1), (b1), and (c1) until the measurement signal for each of the coarse levels have been recorded; and (e1) setting the initial level of the drive power to the coarse level that corresponds to a desired mapping of measurement signal levels to concentrations of ionizable gases.

2. The process of claim 1, wherein changing the drive power in step (c) changes the drive power by less than a difference between the initial level and a next higher one of the coarse levels.

3. The process of claim 1, wherein repeating steps (c), (d), and (e) between the consecutive calibrations of the detector ends when an accumulation of changes in step (c) is equal to or greater than a difference between the initial level and a next higher one of the coarse levels.

* * * * *